United States Patent [19]

Terada et al.

[11] Patent Number: 4,622,421
[45] Date of Patent: Nov. 11, 1986

[54] PHENYLALKANOIC ACID DERIVATIVES AND THEIR USE

[75] Inventors: Atsusuke Terada; Shunji Naruto; Yoshio Iizuka, all of Hiromachi, Japan

[73] Assignee: Sankyo Company Limited, Tokyo, Japan

[21] Appl. No.: 798,236

[22] Filed: Nov. 14, 1985

Related U.S. Application Data

[62] Division of Ser. No. 600,372, Apr. 16, 1984.

[30] Foreign Application Priority Data

Apr. 21, 1983 [JP] Japan .................................. 58-70794

[51] Int. Cl.$^4$ .................. C07C 59/54; C07C 69/73
[52] U.S. Cl. ..................................... 562/491; 560/57; 514/570; 562/459; 260/501.1
[58] Field of Search .......................... 562/491; 560/57; 514/570; 260/501.1

[56] References Cited

U.S. PATENT DOCUMENTS 4,161,538  7/1979  Terada et al. .................. 560/51
4,400,534  8/1983  Terada et al. .................. 560/51

FOREIGN PATENT DOCUMENTS 358018    7/1978  Austria .
2814556  12/1978  Fed. Rep. of Germany .

Primary Examiner—Paul J. Killos
Attorney, Agent, or Firm—Frishauf, Holtz, Goodman & Woodward

[57] ABSTRACT

Compounds of formula (I):

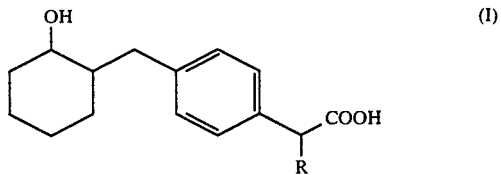

(wherein R represents hydrogen or a $C_1$–$C_3$ alkyl group) have analgesic, anti-inflammatory and immunoregulatory activities. The compounds exist in the form of cis- and trans-isomers with respect to the cyclohexyl ring, as well as a number of optical isomers.

20 Claims, No Drawings

PHENYLALKANOIC ACID DERIVATIVES AND THEIR USE

This is a division of application Ser. No. 600,372 filed Apr. 16, 1984.

BACKGROUND OF THE INVENTION

The present invention relates to a new series of phenylalkanoic acid derivatives, which have been found to have anti-inflammatory and analgesic activities and some of which have also been found to have immuno-regulatory activity. The invention also provides methods of using these compounds.

Mild analgesic and anti-inflammatory agents are amongst the most commonly used of drugs. Most such drugs in common use have side effects which may be distressing or even dangerous to a small percentage of the population—even though the number of people so afflicted may be statistically insignificant, it is better for such persons to employ a different analgesic or anti-inflammatory drug, whose side effects may not be distressing or dangerous to them, rather than to continue with the original drug. There is, therefore, a continuing need for new analgesic and anti-inflammatory drugs, to broaden the choice available to the consumer.

The known mild analgesic and anti-inflammatory agents fall into a number of recognised chemical classes; one such class consists of phenylalkanoic acid derivatives, which mainly vary in accordance with the nature of the substituents on the phenyl group. A series of compounds within this class is disclosed, for example, in British Patent Specification No. 2,113,214 and another such series is disclosed in U.S. Pat. No. 4,400,534.

BRIEF SUMMARY OF THE INVENTION

It is an object of the present invention to provide a series of new phenylalkanoic acid derivatives having good analgesic and anti-inflammatory activities.

The compounds of the present invention are those compounds of formula (I):

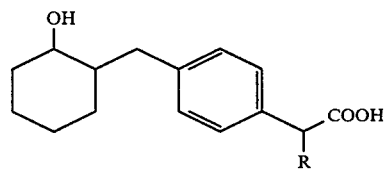

(wherein R represents hydrogen or a $C_1$-$C_3$ alkyl group) and pharmaceutically acceptable salts and esters thereof.

The invention also provides a method of treating a mammal by administering thereto an analgesic and anti-inflammatory agent of the compound (I).

The invention still further provides a method of regulating the immune system of a mammal by administering thereto an immuno-regulatory drug, wherein said immuno-regulatory drug is selected from the compounds of the invention.

DETAILED DESCRIPTION OF INVENTION

The compounds of the invention can exist in the form of geometric isomers, depending upon the relative positions of the substituents on the cyclohexane ring and the present invention contemplates the individual isolated isomers, as well as mixtures thereof, specifically, the cis-isomer, which may be represented by the formula (II):

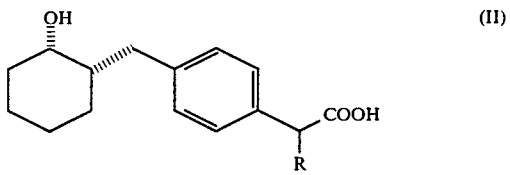

and the trans-isomer, which may be represented by the formula (III):

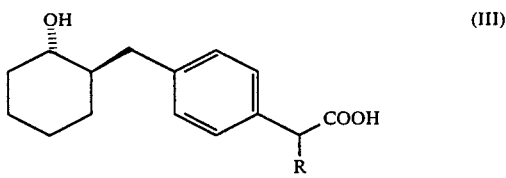

(wherein R is a defined above), as well as pharmaceutically acceptable salts and esters thereof.

Each of these geometric isomers also exists in the form of two optical isomers, which may be separated from each other by conventional resolution techniques or may be left unresolved.

Additionally, the presence of an asymmetric carbon atom adjacent the carboxyl group in the compounds of the invention means that each of the compounds represented by the above formulae can exist in the form of optical isomers, and the present invention contemplates the use of mixtures of these optical isomers, as well as the individual optical isomers. Individual optical isomers can be isolated by conventional optical resolution techniques.

In the compounds of the invention, R represents an alkyl group having from 1 to 3 carbon atoms, and these groups may be straight or branched chain groups, specifically the methyl, ethyl, propyl and isopropyl groups. These compounds of formulae (I), (II) and (III) in which R represents a methyl group are most preferred.

The compounds of the invention may also exist in the form of salts of the compounds represented by formulae (I), (II) and (III). The nature of the salts is not critical to the invention although, of course, since they are intended for therapeutic administration, the salts should be pharmaceutically acceptable salts. Examples of such salts include the alkali and alkaline earth metal salts (such as the sodium or calcium salts), the aluminium salt, the ammonium salt, salts with organic amines (such as triethylamine, dicyclohexylamine, dibenzylamine, morpholine, piperidine or N-ethylpiperidine) and salts with basic amino acids (such as lysine or arginine). The salts may be prepared from the free carboxylic acids of the above formulae by conventional salification processes.

The compounds of the present invention also include the esters of compounds of formulae (I), (II) and (III). Examples of such esters include $C_1$-$C_6$ alkyl esters, aralkyl esters and pyridylmethyl esters. Examples of alkyl ethers include the methyl, ethyl, propyl, isopropyl, bufyl, isobutyl, pentyl, isopentyl, hexyl and isohexyl esters; of these, $C_1$-$C_4$ alkyl esters are preferred, particularly the ethyl, methyl, propyl, isopropyl and butyl esters. Examples of aralkyl esters include the benzyl and phenethyl esters, in which the aromatic ring may be substituted or unsubstituted. Where it is substituted, the substituents may be one or more of the following: $C_1$–$C_6$ groups, e.g. methyl, ethyl, propyl or isopropyl groups; $C_1$–$C_6$ alkoxy groups, e.g. methoxy, ethoxy, propoxy or isopropoxy groups; halogen atoms, e.g. fluorine, chlorine or bromine atoms; or trifluoromethyl groups. In the case of pyridylmethyl esters, these may be the 2-, 3- or 4-pyridylmethyl esters.

Compounds of the invention may be prepared by the following methods.

METHOD A

This is illustrated by the following reaction scheme:

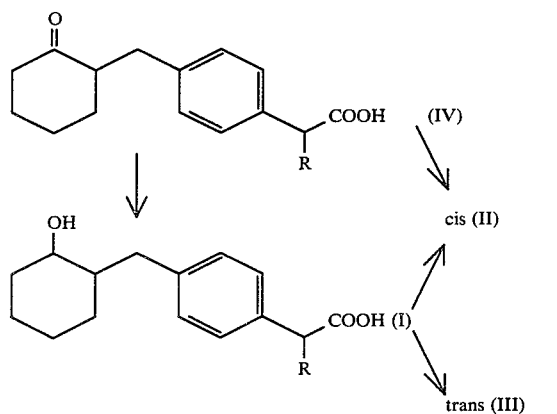

In this, a compound of formula (IV) is reduced to give the compound of formula (I), which may then, if desired, be separated into the cis- and trans-isomers (II) and (III); alternatively, the cis-isomer can be prepared directly from the compound of formula (IV) by appropriate choice of reducing agent.

The reduction reaction is preferably carried out in the presence of an organic solvent, the nature of which is not critical, provided that it does not interfere with the reaction. Examples include ethers (such as tetrahydrofuran or diethyl ether) and aromatic hydrocarbons (such as benzene or toluene).

There is also no particular limitation as to the nature of the reducing agent employed, provided that it only reduces the keto group of the keto-carboxylic acid compound of formula (IV). Suitable reducing agents include alkali metal borohydrides, such as sodium borohydride, sodium cyanoborohydride, potassium tri-sec-butylborohydride and lithium tri-sec-butylborohydride. The potassium tri-sec-butylborohydride or lithium tri-sec-butylborohydride is preferably employed as the tetrahydrofuran solution thereof sold by Aldrich Chemical Co., Inc., under the respective registered trade marks K-Selectride or L-Selectride.

When the reducing agent is sodium cyanoborohydride, the reaction is preferably effected at a pH value of about 3. the reaction temperature is not particularly critical and the reaction can be effected at temperatures ranging from that achieved by ice-cooling to the reflux temperature of the solvent employed. The time required for the reaction will depend upon various factors, mainly the reaction temperature and the nature of the reducing agent used. It is usually from 10 minutes to 3 hours. After completion of the reaction, the compound of formula (I), in the form of a mixture of the cis- and trans-isomers, can be separated from the reaction mixture by conventional means.

The cis- and trans-isomers can be separated from each other by conventional techniques, most especially by high pressure liquid chromatography.

If a tri-sec-butylborohydride such as K-Selectride or L-Selectride is used as the reducing agent, a relatively low temperature is preferably employed, e.g. from −78° C. to the temperature of ice-cooling. The time required for the reaction will depend mainly upon the reaction temperature and the nature of the reducing agent, being generally from 10 minutes to 5 hours. This reduction selectively gives the cis-isomer (II), which can be separated from the reaction mixture by conventional means after completion of the reaction.

METHOD B

This is illustrated by the following reaction scheme:

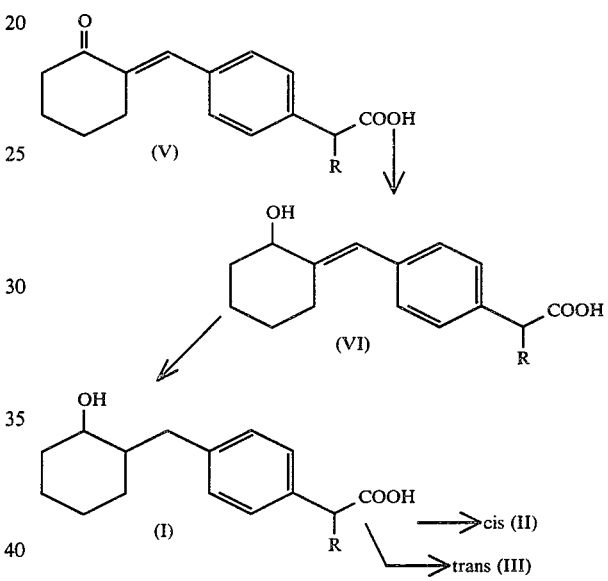

In this reaction, the keto compound of formula (V) is first reduced to the corresponding hydroxy compound, using the same reagents and under the same conditions as described in Method A. The resulting hydroxy compound of formula (VI) is then subjected to catalytic reduction, using hydrogen and a catalyst such as palladium chloride or platinum chloride. This reaction is preferably effected in the presence of a solvent, the nature of which is not critical, provided that it has no adverse effect upon the reaction. Suitable solvents include esters (such as ethyl acetate), aromatic hydrocarbons (such as benzene or toluene) and alcohols (such as methanol or ethanol).

After completion of the reaction, the desired compound of formula (I), in the form of a mixture of its cis- and trans-isomers, may be separated from the reaction mixture by conventional means. As in Method A, the cis- and trans-isomers may be separated from each other by conventional techniques, especially high pressure liquid chromatography.

The compounds of the invention have been tested for pharmacological activity and found to exhibit anti-inflammatory, analgesic and immuno-regulatory activities. Details of the pharmacological tests are as follows:

CARRAGEENIN OEDEMA TEST FOR ANTI-INFLAMMATORY ACTIVITY

Male Wistar rats weighing 120–150 g were fasted overnight and then received a test compound per os as an aqueous tragacanth suspension. 30 minutes later, inflammation was induced by the subcutaneous injection of 0.05 ml of a 1% w/v carrageenin suspension into the plantar tissue of a hind paw of each rat [Winter et al., Proc. Soc. Exp. Biol. Med., 111, 544 (1962)]. The anti-oedema activity was measured volumetrically, by assessing the response, as calculated from the following equation:

$$\text{Response} = (V - V_o)/V_o$$

where $V_o$ and $V$ represent, respectively, the paw volume immediately before and 3 hours after the carrageenin injection. The test compounds were administered at various doses and the results are reported in the following Table as the $ID_{50}$, that is the inhibitory does required to inhibit the response by 50%.

PAIN TEST FOR ANALGESIC ACTIVITY

This test was conducted according to a modification of the method reported by L. O. Randall and J. J. Selitto in Arch. Int. Pharmacodyn., 11, 409 (1959), proposed by Winter and Flatake (1957).

Male Wistar-Imamichi rats of 4 weeks of age and weighing 60–90 g were injected with 0.1 ml of a 20% by weight suspension of Brewers' yeast in the right hind paw. 4 hours later, rats which had a pain threshold to pressure-induced pain less than 10×30 g were selected. Each of these was given orally a test compound as an aqueous tragacanth suspension. 1 and 2 hours after administration of the test compound, the pain threshold was determined by observing pain responses (such as struggling or squeaking) when the inflamed or normal paw was subjected to pressure by a machine (Ugo-Basile). An "effective" animal was defined, in accordance with Blane's method (1968), as an animal which showed at least twice the mean pain threshold of control animals. The $ED_{50}$ was calculated by the method of Litchfield and Wilcoxon (1949).

The compounds tested are identified in the Table as follows:

1 = (±)-2-[4-(cis-2-hydroxycyclohexylmethyl)phenyl]propionic acid;
2 = (±)-2-[4-(trans-2-hydroxycyclohexylmethyl)phenyl]propionic acid
3 = Indomethacin;
compounds 1 and 2 being compounds of the invention and compound 3 being a well known mild analgesic and anti-inflammatory agent.

TABLE

| Compound | Anti-inflammatory activity, $ID_{50}$ | Analgesic activity, $ED_{50}$ |
| --- | --- | --- |
| 1 | 3.3 mg/kg | 0.86 mg/kg |
| 2 | 0.96 mg/kg | 0.76 mg/kg |
| 3 | 2.2 mg/kg | 1.6 mg/kg |

From the Table, it can be seen that the compounds of the invention have analgesic and anti-inflammatory activities comparable with or better than the activity of Indomethacin.

TEST FOR IMMUNO-REGULATORY ACTIVITY

The immuno-regulatory activity of (±)-2-[4-(cis-2-hydroxycyclohexylmethyl)phenyl]propionic acid was tested by Cunningham's method [A. J. Cunningham and A. Szenberg, Immunology 14, 599 (1968)]. The test compound was administered orally to female mice of the BALB/c strain and simultaneously sheep erythrocytes were administered intraperitonially, in order to sensitise the animal to these erythrocytes as an antigen. After 5 days, the spleen of the experimental animal was extracted and the number of IgM antibody-producing cells in the spleen cells was calculated. The percent inhibition of antibody production was found to be 50% or more when the dose of compound administered was from 1 to 10 mg per kg.

These results demonstrate that the compounds of the invention have valuable analgesic, anti-inflammatory and immuno-regulatory activities.

The compounds of the invention are preferably administered in admixture with a carrier or diluent in the form of a conventional pharmaceutical composition, preferably formulated for oral, rectal or topical administration. Compositions for oral administration may be formulated as, for example, tablets, capsules, granules, powders or syrups, compositions for rectal administration may be in the form of suppositories and compositions for topical administration may be in the form of an ointment or a cream. The dosage employed will vary depending upon the condition, age and body weight of the patient as well as the chosen route of administration, but usually the dose for oral administration to an adult human being would be from 50 to 300 mg per day, which may be administered in a single dose or in divided doses.

The preparation of the compounds of the invention is further illustrated by the following Examples.

EXAMPLE 1

(±)-2-[4-(2-hydroxycyclohexylmethyl)phenyl]propionic acid 720 mg of (±)-2-[4-(2-oxocyclohexylmethyl)phenyl]propionic acid were dissolved in 15 ml of tetrahydrofuran, and then 400 mg of sodium cyanoborohydride were added to the solution. The resulting mixture was stirred for 40 minutes under ice-cooling, while maintaining the pH at a value of 3 by the addition of 3N methanolic hydrochloric acid. Ice-water was then added to the reaction mixture, which was extracted with diethyl ether. The extract was dried over anhydrous sodium sulphate and the solvent was distilled off to give 690 mg of a mixture of the trans- and cis-isomers. This mixture was subjected to high pressure liquid chromatography through silica gel deactivated with acetic acid, using a 1:1 by volume mixture of ethyl acetate and hexane as eluent. The cis-isomer was eluted first, followed by the trans-isomer. Each isomer was recrystallised from a mixture of diethyl ether and hexane and obtained in the form of crystals.

(±)-2-[4-(trans-2-Hydroxycyclohexylmethyl)phenyl]propionic acid

Melting at 117°–120° C.

Elemental analysis: Calculated for $C_{16}H_{22}O_3$: C, 73.25%; H, 8.45%. Found: C, 73.24%; H, 8.40%.

(±)-2-[4-(cis-2-Hydroxycyclohexylmethyl)phenyl]propionic acid

Melting at 130°–133° C.

Elemental analysis: Calculated for $C_{16}H_{22}O_3$: C, 73.25%; H, 8.45%. Found: C, 73.20%; H, 8.43%.

EXAMPLE 2

(±)-2-[4-(2-Hydroxycyclohexylmethyl)phenyl]propionic acid 2.0 g of (+)-2-[4-(2-oxocyclohexylidenemethyl)phenyl]propionic acid and 0.6 g of sodium cyanoborohydride were dissolved in 50 ml of methanol. The pH of the mixture was adjusted to a value of 3 with 6N hydrochloric acid, whilst ice-cooling. The mixture was then stirred, with heating, for 40 minutes. Ice-water was added to the reaction mixture, which was then extracted with diethyl ether. The extract was washed with water and dried over anhydrous sodium sulphate, and the solvent was distilled off, to give 350 mg of (±)-2-[4-(2-hydroxycyclohexylidenemethyl)phenyl]propionic acid as crystals [compound of formula (VI)]. These crystals were dissolved in 10 ml of ethyl acetate, 50 mg of palladium chloride were added, and the mixture was subjected to catalytic reduction whilst bubbling hydrogen through the mixture. After the theoretical amount of hydrogen had been absorbed, the catalyst was removed by filtration and the solvent was distilled off, to give 330 mg of a mixture of the cis- and trans-isomers. This mixture was treated in the same manner as in Example 1, affording crystals of the cis- and trans-isomers of the title compound, having the same properties as the product of Example 1.

EXAMPLE 3

(±)-2-[4-(cis-2-Hydroxycyclohexylmethyl)phenyl]propionic acid 10.0 g of (±)-2-[4-(2-oxocyclohexylmethyl)phenyl]propionic acid were dissolved in 150 ml of tetrahydrofuran. The solution was cooled to −78° C. and, whilst maintaining the solution at this temperature and under a stream of nitrogen, 200 ml of K-Selectride (as a 0.5 molar tetrahydrofuran solution) were added dropwise. When the whole of the K-Selectride had been added, the reaction mixture was stirred for 1 hour at 0° C., after which it was cooled to −10° C. and 400 ml of a 0.5N solution of hydrochloric acid was added through a dropping funnel. The reaction mixture was stirred for 1 hour, after which it was extracted with diethyl ether. The extract was washed with water and dried over anhydrous sodium sulphate. The solvent was distilled off, giving 10.5 g of the title compound in the form of crystals. These were recrystallised from a mixture of diethyl ether and hexane, giving the title compound as pure crystals melting at 130°–133° C.

Elemental analysis: Calculated for $C_{16}H_{22}O_3$: C, 73.25%; H, 8.45%. Found: C, 73.22%; H, 8.45%.

We claim:

1. Compounds of formula (I):

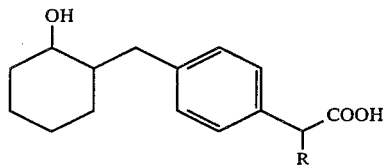

(I)

(wherein R represents hydrogen or a $C_1$–$C_3$ alkyl group) and pharmaceutically acceptable salts and esters thereof.

2. Compounds as claimed in claim 1, wherein R represents the methyl group.

3. Compounds as claimed in claim 1, wherein said salt is selected from the group consisting of alkali metal, alkaline earth metal, aluminium, ammonium, organic base and amino acid salts.

4. Compounds of formula:

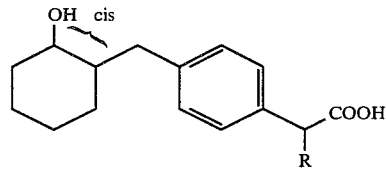

(wherein R represents hydrogen or a $C_1$–$C_3$ alkyl group) and pharmaceutically acceptable salts and esters thereof.

5. Compounds as claimed in claim 4, wherein R represents the methyl group.

6. Compounds as claimed in claim 4, wherein said salt is selected from the group consisting of alkali metal, alkaline earth metal, aluminium, ammonium, organic base and amino acid salts.

7. Compounds of formula:

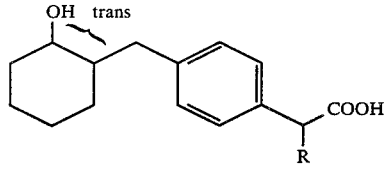

(wherein R represents hydrogen or a $C_1$–$C_3$ alkyl group) and pharmaceutically acceptable salts and esters thereof.

8. Compounds as claimed in claim 7, wherein R represents the methyl group.

9. Compounds as claimed in claim 7, wherein said salt is selected from the group consisting of alkali metal, alkaline earth metal, aluminium, ammonium, organic base and amino acid salts.

10. A method of treating a mammal by administering thereto an analgesic and anti-inflammatory agent, wherein said agent is selected from the group consisting of compounds of formula (I):

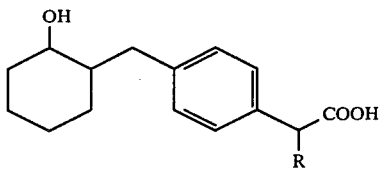

(wherein R represents hydrogen or a $C_1$–$C_3$ alkyl group) and pharmaceutically acceptable salts and esters thereof.

11. The method as claimed in claim 10, wherein R represents the methyl group.

12. The method as claimed in claim 10, wherein said salt is selected from the group consisting of alkali metal, alkaline earth metal, aluminium, ammonium, organic base and amino acid salts.

13. The method as claimed in claim 10, wherein said compound is in the cis-configuration with respect to the cyclohexyl ring.

14. The method as claimed in claim 10, wherein said compound is in the trans-configuration with respect to the cyclohexyl ring.

15. The method as claimed in claim 10, wherein said compound is selected from the group consisting of (±)-2-[4-(cis-2-hydroxycyclohexylmethyl)phenyl]propionic acid and salts and esters thereof.

16. The method as claimed in claim 10, wherein said compound is selected from the group consisting of (±)-2-[4-(trans-2-hydroxycyclohexylmethyl)phenyl]propionic acid and salts and esters thereof.

17. The method as claimed in claim 10, wherein said mammal is human.

18. The method as claimed in claim 10 wherein said agent is (±)-2-[4-(trans-2-hydroxy-cyclohexylmethyl)phenyl]propionic acid.

19. The compound of claim 1 which is (±)-2-[4-(cis-2-hydroxy-cyclohexylmethyl)phenyl]propionic acid.

20. The compound of claim 1 which is (±)-2-[4-(trans-2-hydroxy-cyclohexylmethyl)phenyl]propionic acid.

* * * * *

UNITED STATES PATENT AND TRADEMARK OFFICE
CERTIFICATE OF CORRECTION

PATENT NO. : 4,622,421
DATED : November 11, 1986
INVENTOR(S) : Atsusuke Terada, et al It is certified that error appears in the above-identified patent and that said Letters Patent is hereby corrected as shown below:

On the title page of the patent, under the heading FOREIGN PATENT DOCUMENTS, add the following foreign publication:

-- 2113214        8/1983        United Kingdom --.

Signed and Sealed this

Twenty-ninth Day of August, 1989

*Attest:*

DONALD J. QUIGG

*Attesting Officer*    *Commissioner of Patents and Trademarks*